(12) United States Patent
Kim et al.

(10) Patent No.: US 8,827,260 B2
(45) Date of Patent: Sep. 9, 2014

(54) APPARATUS FOR DETECTING A FOREIGN SUBSTANCE ON AN INTERLEAVING PAPER TO BE INSERTED BETWEEN GLASS SUBSTRATES

(71) Applicant: Samsung Corning Precision Materials Co., Ltd., Gyeongsangbuk-do (KR)

(72) Inventors: Misun Kim, ChungCheongNam-Do (KR); Hyun Woo Kim, ChungCheongNam-Do (KR); Siho Seong, ChungCheongNam-Do (KR); YoungJoong Kim, ChungCheongNam-Do (KR); Taeho Keem, ChungCheongNam-Do (KR)

(73) Assignee: Samsung Corning Precision Materials Co., Ltd. (KR)

( * ) Notice: Subject to any disclaimer, the term of this patent is extended or adjusted under 35 U.S.C. 154(b) by 0 days.

(21) Appl. No.: 13/628,595

(22) Filed: Sep. 27, 2012

(65) Prior Publication Data

US 2014/0070483 A1    Mar. 13, 2014

(30) Foreign Application Priority Data

Sep. 13, 2012  (KR) .......................... 10-2012-0101700

(51) Int. Cl.
*B65H 5/02* (2006.01)
(52) U.S. Cl.
USPC .............................................. 271/12; 271/98
(58) Field of Classification Search
USPC ....................... 271/90, 98, 265.01, 12; 269/21
See application file for complete search history.

(56) References Cited

U.S. PATENT DOCUMENTS

| | | | | | |
|---|---|---|---|---|---|
| 3,907,127 | A | * | 9/1975 | Bollinger et al. | 414/788.9 |
| 4,391,439 | A | * | 7/1983 | Edstrom | 271/90 |
| 4,960,361 | A | * | 10/1990 | Melzer | 414/801 |
| 6,182,957 | B1 | * | 2/2001 | Becker | 269/21 |
| 6,904,844 | B2 | * | 6/2005 | Koizumi et al. | 101/477 |
| 6,910,687 | B1 | * | 6/2005 | Van Nice et al. | 271/98 |
| 7,044,056 | B2 | * | 5/2006 | Miyoshi | 101/477 |
| 7,051,653 | B2 | * | 5/2006 | Ono | 101/477 |
| 7,152,531 | B2 | * | 12/2006 | Miyoshi | 101/477 |
| 7,322,574 | B2 | * | 1/2008 | Van Nice et al. | 271/12 |
| 7,715,615 | B2 | * | 5/2010 | Van Nice et al. | 382/149 |
| 8,056,895 | B2 | * | 11/2011 | Yuen et al. | 271/105 |

* cited by examiner

*Primary Examiner* — Kaitlin Joerger
(74) *Attorney, Agent, or Firm* — Lerner, David, Littenberg, Krumholz & Mentlik, LLP

(57) ABSTRACT

An apparatus for detecting a foreign substance on an interleaving paper to be inserted between glass substrates, in which the process of detecting the foreign substance on the paper is automated to improve the detection efficiency. The apparatus includes a paper-loading unit and a paper-inspecting unit configured to be connected to the paper-loading unit. The paper-inspecting unit detects a foreign substance on a surface of the paper loaded by the paper-loading unit. The apparatus also includes a paper-unloading unit, which is configured to be connected to the paper-inspecting unit, and unloads the paper from the paper-inspecting unit and then stacks the paper. The apparatus also includes a controller, which controls the paper-loading unit, the paper-inspecting unit and the paper-unloading unit to transfer the paper, and controls the paper-inspecting unit to detect the foreign substance.

8 Claims, 4 Drawing Sheets

APPARATUS FOR DETECTING A FOREIGN SUBSTANCE ON AN INTERLEAVING PAPER TO BE INSERTED BETWEEN GLASS SUBSTRATES

CROSS REFERENCE TO RELATED APPLICATION

The present application claims priority from Korean Patent Application Number 10-2012-0101700 filed on Sep. 13, 2012, the entire contents of which application are incorporated herein for all purposes by this reference.

BACKGROUND OF THE INVENTION

1. Field of the Invention

The present invention relates to an apparatus for detecting a foreign substance on an interleaving paper to be inserted between glass substrates, and more particularly, to an apparatus for detecting a foreign substance on an interleaving paper to be inserted between glass substrates, in which the process of detecting the foreign substance is automated to improve the detection efficiency.

2. Description of Related Art

In general, a surface of glass substrates that are used for flat panel displays, such as plasma display panels (PDPs) or liquid crystal displays (LCDs), are vulnerable to being scratched or contaminated when the glass substrates are stored or carried. In particular, in the case of glass substrates, such as a non-alkali glass substrate used for an LCD, in which an electrical circuit or the like is embedded in the surface of glass substrates, even a small scratch or insignificant contaminant on the surface can cause a disconnection of wire or a patterning defect.

In many cases, scratches occur on the surface of a glass substrate due to its misalignment with an adjacent glass substrate when glass substrates are stored such that they are stacked on each other or carried. In addition, glass substrates are frequently contaminated when a foreign substance, such as organic matter, become attached to the surface of the glass substrates. This is problematic because such organic matter is not easily removed from the surface of the glass substrates by cleaning with water.

In order to overcome this problem, an interleaving paper is interposed between adjacent glass substrates in order to separate the adjacent glass substrates from each other. However, in this case, scales originating from the paper, e.g., scales of a paper additive (kaolinite) such as aluminum silicate, are transferred to the surface of the glass substrates, thereby contaminating the glass substrates. Accordingly, in the related art, the quality of glass substrates is managed by individually detecting a foreign substance attached to the paper, using the human eyes. However, since the requirement of the interleaving paper between adjacent substrates is gradually increasing, it is becoming more difficult to inspect a large number of interleaving papers using the human eyes. It is also difficult to guarantee the reliability of the quality of the paper that is interposed between adjacent substrates, because the ability to detect a foreign substance varies depending on each individual inspector.

The information disclosed in this Background of the Invention section is only for the enhancement of understanding of the background of the invention, and should not be taken as an acknowledgment or any form of suggestion that this information forms a prior art that would already be known to a person skilled in the art.

BRIEF SUMMARY OF THE INVENTION

Various aspects of the present invention provide an apparatus for detecting a foreign substance on an interleaving paper to be interposed between glass substrates, in which the process of detecting the foreign substance on the paper is automated to improve the detection efficiency.

In an aspect of the present invention, provided is an apparatus for detecting a foreign substance on an interleaving paper to be inserted between glass substrates. The apparatus includes a paper-loading unit and a paper-inspecting unit configured to be connected to the paper-loading unit. The paper-inspecting unit detects a foreign substance on a surface of the paper loaded by the paper-loading unit. The apparatus also includes a paper-unloading unit, which is configured to be connected to the paper-inspecting unit, and unloads the interleaving paper from the paper-inspecting unit and stacks the interleaving paper. The apparatus also includes a controller, which controls the paper-lading unit, the paper-inspecting unit and the paper-unloading unit to transfer the paper, and controls the paper-inspecting unit to detect the foreign substance.

In an exemplary embodiment, the paper-loading unit may include a paper supply unit, which supplies the paper, and a paper-feeding unit disposed adjacent to the paper supply unit. The paper-feeding unit transfers the paper, which is supplied by the paper supply unit, to the paper-inspecting unit.

In an exemplary embodiment, the apparatus may further include a suction pad, which picks up one sheet of the paper at a time.

In addition, the paper-feeding unit may transfer the paper to the paper-inspecting unit using rollers.

Furthermore, the paper-feeding unit may include a detection sensor, which senses or counts the number of sheets of the paper to be transferred to the paper-inspecting unit.

In an exemplary embodiment, the paper-inspecting unit may include a table, which holds the paper seated thereon by suction, and an inspection head disposed on the table. The inspection head detects a foreign substance on the surface of the paper while sliding in the direction orthogonal to the direction in which the paper proceeds in such a manner that the inspection head is spaced apart from the surface of the paper.

In an exemplary embodiment, the paper-unloading unit may include a paper discharge unit, a paper guide rail, a paper carrier unit and a tray. The paper discharge unit discharges the paper from the paper-inspecting unit. The paper guide rail guides the paper from the paper discharge unit to the paper carrier unit. The paper carrier unit carries the paper to the tray and stacks the paper on the tray.

In an exemplary embodiment, the apparatus may further include a display unit, which receives an inspection result from the paper-inspecting unit and displays the inspection result on a screen.

According to embodiments of the invention, the process of inspecting the paper to be used for a glass substrate, including the steps of aligning, supplying, feeding, inspecting, discharging and stacking the paper, is automated. It is possible to increase the detection efficiency compared to a related art, in which inspection is performed visually and to significantly reduce the amount of time that is spent in checking for a foreign substance on the paper, thereby significantly reducing the number of inspectors.

In addition, according to embodiments of the invention, it is possible to input the coordinates and types of attached a foreign substance into a database. Accordingly, it is possible to reduce the incidence of defects on glass substrates that are caused by a foreign substance on the paper, and thus establish a long-term quality management system for the paper.

The methods and apparatuses of the present invention have other features and advantages which will be apparent from, or are set forth in greater detail in the accompanying drawings, which are incorporated herein, and in the following Detailed Description of the Invention, which together serve to explain certain principles of the present invention.

DETAILED DESCRIPTION OF THE INVENTION

Reference will now be made in detail to various embodiments of the present invention, examples of which are illustrated in the accompanying drawings and described below, so that a person having ordinary skill in the art to which the present invention relates can easily put the present invention into practice.

In the following description of the present invention, detailed descriptions of known functions and components incorporated herein will be omitted when they may make the subject matter of the present invention unclear.

With reference to FIG. 1 to FIG. 5, a description will be given below of an apparatus for detecting a foreign substance on an interleaving paper to be inserted between glass substrates according to an embodiment of the invention.

Figure 1:
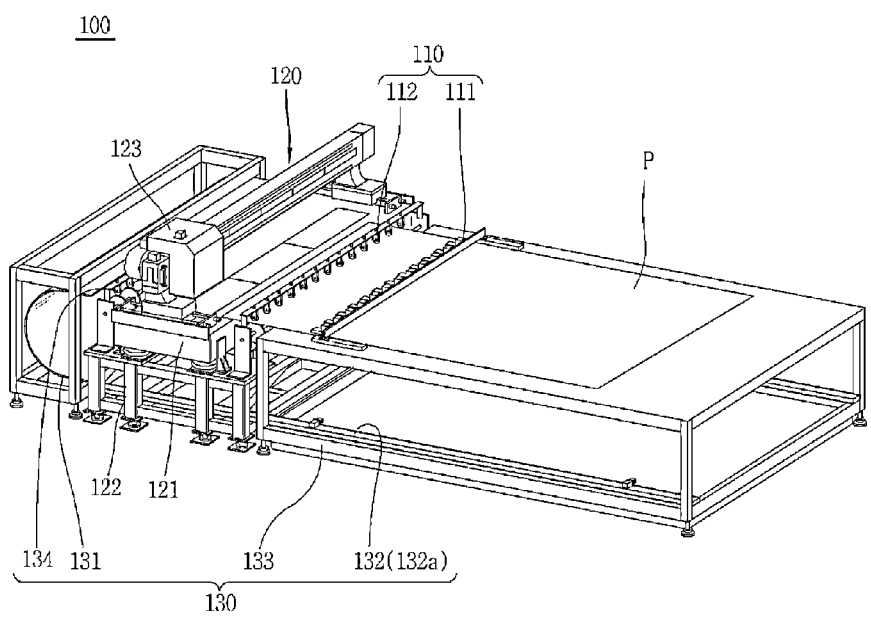
FIG. 1 is a perspective view schematically showing an apparatus for detecting a foreign substance on an interleaving paper for a glass substrate according to an embodiment of the invention.

As shown in FIG. 1, the apparatus 100 for detecting a foreign substance on an interleaving paper according to an embodiment of the invention is an apparatus that is used to check for a foreign substance on the surface of an interleaving paper P, which is inserted between adjacent glass substrates in order to separate their surfaces from each other when the glass substrates are stacked on each other. The apparatus 100 for detecting a foreign substance on a paper (hereinafter, also referred to as "detection apparatus") includes a paper-loading unit 110, a paper-inspecting unit 120, a paper-unloading unit 130 and a controller (not shown).

Figure 2:
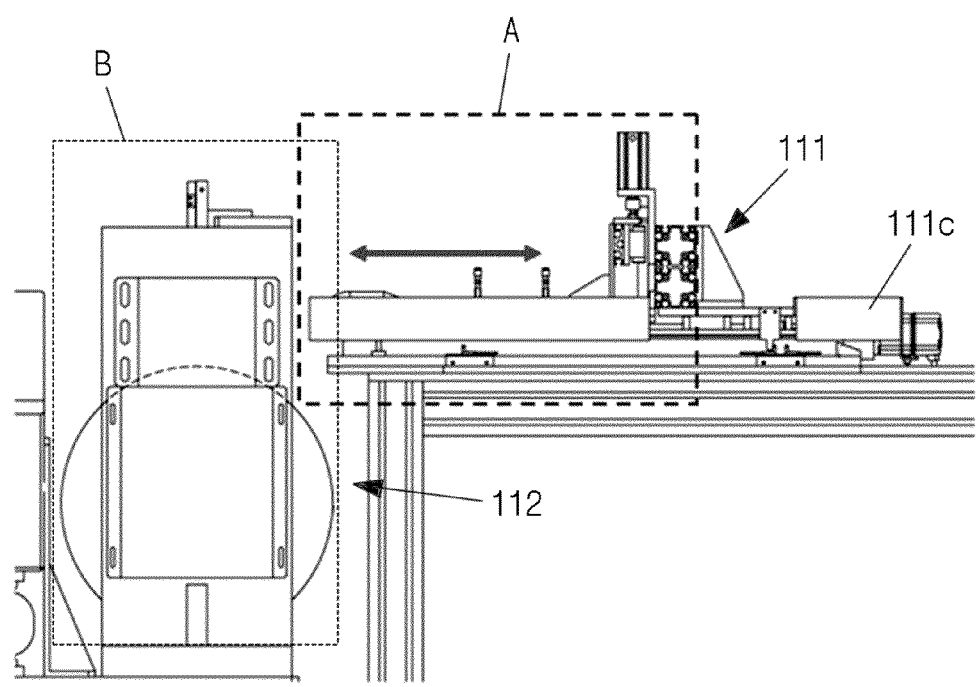
FIG. 2 is a detailed cross-sectional view showing a paper-loading unit of the apparatus for detecting a foreign substance on an interleaving paper for a glass substrate according to an embodiment of the invention.
Figure 3:
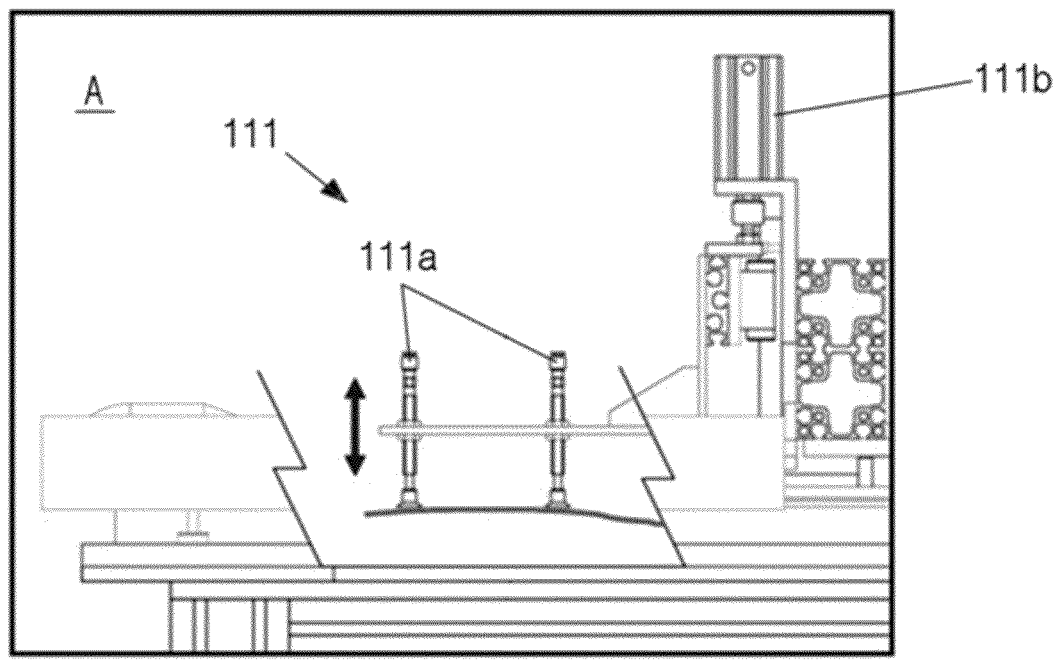
FIG. 3 is an enlarged view of part "A" of FIG. 2.

The paper-loading unit 110 is a device that loads the paper P that is to be inspected. Referring to FIG. 2, the paper-loading unit 110 may include a paper supply unit 111 and a paper-feeding unit 112. Referring to FIG. 2 and FIG. 3, the paper supply unit 111 supplies a plurality of sheets of paper P to the paper-feeding unit 112. Since the inspection on the paper P is carried out one sheet at a time, the paper supply unit 111 may be provided with at least one suction pad 111a, which holds the paper P. An up/down motor 111b is connected to the suction pad 111a such that it can reciprocally move the suction pad 111a, to which the paper P is attached, upward and downward. The paper P, which is held by the suction pad 111a, can be transferred by a forward/backward motor 111c, which is connected to the suction pad 111a.

Figure 4:
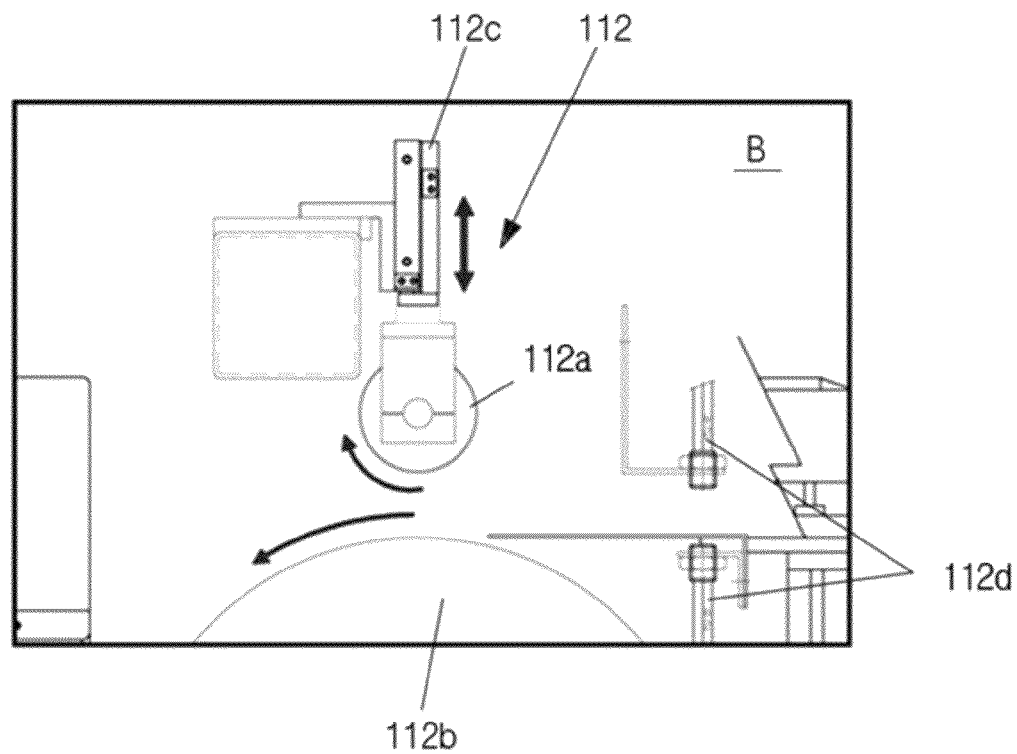
FIG. 4 is an enlarged view of part "B" of FIG. 2.

In addition, as shown in FIG. 2 and FIG. 4, the paper-feeding unit 112 is provided adjacent to the paper supply unit 111, particularly, adjacent to the front portion of the paper supply unit 111 with respect to the direction in which the paper P proceeds. The paper-feeding unit 112 serves to transfer the paper P, which is supplied one sheet at a time via the paper supply unit 111, to the paper-inspecting unit 120. For this, the paper-feeding unit 112 can transfer the paper P, which is supplied by the paper supply unit 111, to the paper-inspecting unit 120 using rollers. As shown in FIG. 4, the paper-feeding unit 112 includes an idle roller 112a, which can be moved upward and downward by an up/down motor 112c, and a drive roller 112b, which can be moved under the idle roller 112a. The rotation of the drive roller 112b can make the paper P transferred toward the paper-inspecting unit 120. To transfer the paper P, the idle roller 112a is moved downward, and is then rotated by the rotation of the drive roller 112b, when the paper P is interposed between the idle roller 112a and the drive roller 112b, thereby transferring the paper P forwards. Since the paper P may sag due to gravity in this process of being transferred, it is preferred that the diameter of the drive roller 112b be greater than that of the idle roller 112b. Since the interleaving paper P is thin, several sheets of paper P may be simultaneously held by the suction pad 111a and then introduced to the paper-feeding unit 112. In order to prevent this, detection sensors 112d, which sense or count the number of sheets of paper P, may be provided on the portion where the paper supply unit 111 is connected to the paper-feeding unit 112. As shown in the figures, the detection sensors 112d may be positioned on both sides of the paper P, one being positioned above the paper P and the other one being positioned under the paper P.

Figure 5:
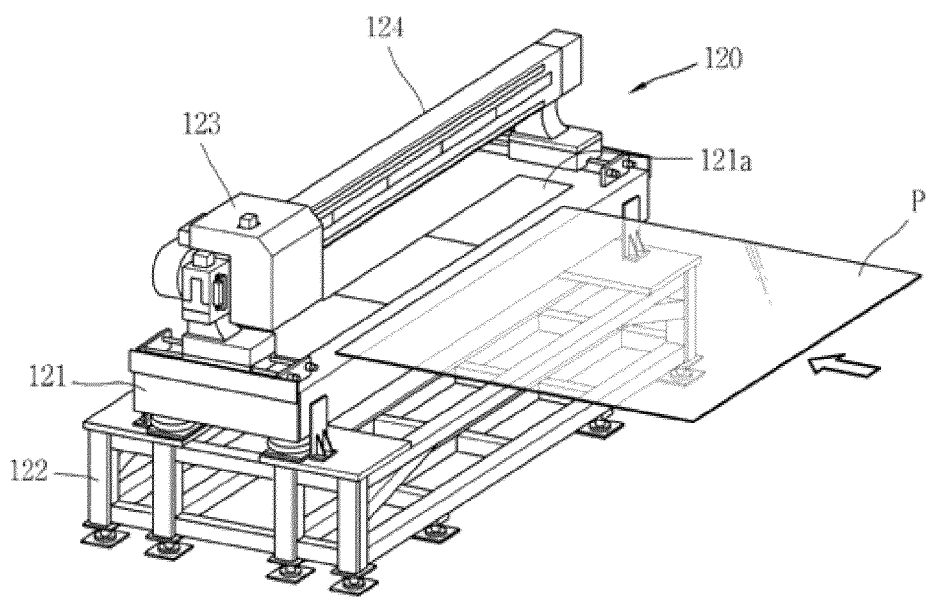
FIG. 5 is a perspective view schematically showing a paper-inspecting unit of the apparatus for detecting a foreign substance on an interleaving paper for a glass substrate according to an embodiment of the invention.

The paper-inspecting unit 120 is a device for checking for a foreign substance on the surface of the paper P, and is configured to be connected to the paper-loading unit 110. Specifically, the paper-inspecting unit 120 is disposed in front of the paper-feeding unit 112 of the paper-loading unit 110 with respect to the direction in which the paper P proceeds. As shown in FIG. 5, the paper-inspecting unit 120 may include a table 121 and an inspection head 123. The paper P is loaded on the table 121 by the paper-loading unit 110. The table 121 may be seated on a support 112, which is composed of separate frames. The table 121 is provided with an air table 121a, which planarizes the paper P by suction so that it can be inspected. It is preferred that the air table 121a also has a corresponding size.

In addition, the inspection head 123 is a device that detects a foreign substance on the surface of the paper P. The inspection head 123 detects a foreign substance while sliding in the lateral direction of the paper P along a guide rail 124, which is provided on the table 121, in such a manner that the inspection head is spaced apart from the surface of the paper P. The guide rail 124 extends in the lateral direction of the table 121, particularly, in the direction orthogonal to the direction in which the paper P proceeds. Although not shown, the inspection head 123 is provided with several components in order to detect a foreign substance on the paper P. These components may include, for example, a particle blower, an edge blower and a paper roller, a scan inspection device, a review inspection device, a marking stamp, a lighting device, etc. The particle blower removes particles from the paper by blowing air thereto. The edge blower and the paper roller planarize the corners and the surface of the paper P by pressing them. A scan inspection device inspects the surface of the paper P. The review inspection device makes a foreign substance detected by the scan inspection device more visible by magnifying it. The marking stamp stamps a mark on the foreign substance.

The lighting device helps the scan inspection device and the review inspection device. However, the inspection head 123 of the invention is not specifically limited to this configuration. The inspection head 123 may detect a foreign substance on the surface of the paper P in a variety of ways. For example, the inspection head may be designed to have the same as or larger than that of the paper, so that the sliding of the inspection head along the width of the paper is not necessary. The inspection head may be configured to slide in the direction that the paper proceeds.

When the detection of a foreign substance on the paper P by the inspection head 123 is completed, the air table 121a performs a blowing, and then, the paper P is transferred forward by a distance equal to the length by which the paper has been inspected, after which the process of checking for a foreign substance on the adjacent portion of the surface is resumed.

Returning to FIG. 1, the paper-unloading unit 130 is a device that unloads, from the paper-inspecting unit, and stacks the paper P, after the detection of a foreign substance on the surface thereof is completed. The paper-unloading unit 130 is configured to be connected to the paper-inspecting unit 120. The paper-unloading unit 130 may include a paper discharge unit 134, a semi-cylindrical paper guide rail 131, a paper carrier unit 132 and a tray 133. The paper discharge unit 134 discharges the paper using rollers in a similar way to the paper-feeding unit. The semi-cylindrical paper guide rail 131 is a device that guides the paper P. As shown in the figures, the paper P is discharged onto the inner surface of the semi-cylindrical paper guide rail 131 by the paper discharge unit 134, and then slides downward along a semicircular path on the inner surface of the semi-cylindrical paper guide rail 131. According to an embodiment of the invention, it is possible to design the detection apparatus 100 to be compact by placing the paper-unloading unit 130 under the paper-loading unit 110 and the paper-inspecting unit 120. This can consequently decrease the distance that workers are required to move, thereby increasing the efficiency of work.

In addition, the paper carrier unit 132 is configured to be connected to the semi-cylindrical paper guide rail 131. The paper carrier unit holds the paper P using, for example, a clamp which can move along the linear rail 132a. Then, the clamp drags it to the end of the tray 133, and then releases it so that the paper is stacked on the tray.

The controller (not shown) serves to control the paper-loading unit 110, the paper-inspecting unit 120 and the paper-unloading unit 130, thereby automatically transferring the paper P. The controller (not shown) controls the inspection head 123 of the paper-inspecting unit 120 to detect a foreign substance on the paper P. Controllers may be provided for the paper-loading unit 110, the paper-inspecting unit 120 and the paper-unloading unit 130, respectively in order to separately control them. Alternatively, only one controller (not shown) may be provided, such that it can control all of the foregoing components. When the process of supplying, inspecting, discharging and stacking the paper P is automatically controlled by the controller (not shown), it is possible to increase the detection efficiency compared to a related art, in which inspection is performed using the human eyes, and to significantly reduce the amount of time spent in checking for a foreign substance on the paper P, thereby significantly reducing the number of inspectors.

Furthermore, an embodiment of the invention may also include a display unit (not shown), which receives an inspection result from the inspection head 123, which is controlled by the controller (not shown), and displays the inspection result on the screen so that a worker can examine it. The display unit (not shown) may be configured as a computer or the like, so that the coordinates and types of foreign substances, which are transmitted from the inspection head 123, can be input into a database. Accordingly, it is possible to reduce defects on glass substrates, which are caused by a foreign substance on the paper P, and thus to establish a long-term quality management system for the paper P.

A description will be given below of the automatic inspection process using the apparatus for detecting a foreign substance on an interleaving paper according to an embodiment of the invention.

First, the paper supply unit operates the suction pad 111a so that it holds the paper P, operates the up/down motor 111b so that the suction pad 111a is moved upward, and then operates the forward/backward motor 111c so that it supplies the paper P into the paper-feeding unit 112. At this time, the detection sensor 112d counts the number of sheets of paper P to be supplied to the drive roller 111. When two or more sheets of paper P are detected, the controller (not shown) receives a corresponding signal from the detection sensor 112d, has the paper P returned backward to the paper supply unit 111 by controlling the forward/backward motor 111c, and picks up a single paper P again by adjusting the suction strength of the suction pad 111a. Afterwards, the controller (not shown) controls the drive roller 111b to transfer the paper P toward the paper-inspecting unit 120.

When the paper P is transferred to the paper-inspecting unit 120 and is placed on the table 121, the controller (not shown) controls the air table 121a to planarize the paper P by suction, and the inspection head 123 inspects the surface of the paper P to check for a foreign substance. Here, the inspection of the paper P is conducted over the entire surface of the paper P in such a way that the paper P is moved by a predetermined length at a time.

When the paper P is discharged from the paper-inspecting unit 120 after being completely inspected, it is guided downward along a semicircular path on the inner surface of the semi-cylindrical paper guide rail. The paper carrier unit 132 carries the paper P to the end of the tray, and then stacks the paper P on the tray 133.

The foregoing descriptions of specific exemplary embodiments of the present invention have been presented with respect to the certain embodiments and drawings. They are not intended to be exhaustive or to limit the invention to the precise forms disclosed, and obviously many modifications and variations are possible for a person having ordinary skill in the art in light of the above teachings.

It is intended therefore that the scope of the invention not be limited to the foregoing embodiments, but be defined by the Claims appended hereto and their equivalents.

What is claimed is:

1. An apparatus for detecting a foreign substance on an interleaving paper to be inserted between glass substrates, comprising:
   a paper-loading unit loading the interleaving paper;
   a paper-inspecting unit configured to be connected to the paper-loading unit, and detecting the foreign substance on a surface of the interleaving paper;
   a paper-unloading unit configured to be connected to the paper-inspecting unit, and unloading, from the paper-inspecting unit, and then stacking the interleaving paper; and
   a controller controlling the paper-loading unit, the paper-inspecting unit and the paper-unloading unit to transfer the interleaving paper and controlling the paper-inspecting unit to detect the foreign substance, wherein the paper-inspecting unit comprises a table provided with an air table which planarizes the interleaving paper seated thereon by suction;

wherein the paper-inspecting unit further comprises an inspection head disposed on the table such that at least an edge blower is provided with the inspection head to planarize one or more corners and the surface of the paper using the edge blower.

2. The apparatus of claim 1, wherein the paper-loading unit comprises:

a paper supply unit, which supplies the interleaving paper; and a paper-feeding unit disposed adjacent to the paper supply unit, and transferring the interleaving paper supplied by the paper supply unit, to the paper-inspecting unit.

3. The apparatus of claim 2, further comprising a suction pad, which picks up one sheet of the interleaving paper at a time.

4. The apparatus of claim 2, wherein the paper-feeding unit transfers the interleaving paper to the paper-inspecting unit using rollers.

5. The apparatus of claim 2, wherein the paper-feeding unit comprises a detection sensor, which counts the number of sheets of the interleaving paper to be transferred to the paper-inspecting unit.

6. The apparatus of claim 1, wherein the inspection head is arranged to detect the foreign substance on the surface of the interleaving paper while sliding in a direction orthogonal to a direction in which the interleaving paper proceeds in such a manner that the inspection head is spaced apart from the surface of the interleaving paper.

7. The apparatus of claim 1, wherein the paper-unloading unit comprises:

a paper discharge unit, a paper guide rail, a paper carrier unit, and a tray the paper discharge unit discharging the interleaving paper from the paper-inspecting unit, the paper guide rail guiding the interleaving paper from the paper discharge unit to the paper carrier unit, and the paper carrier unit carrying the interleaving paper to the tray, and stacking the interleaving paper on the tray.

8. The apparatus of claim 1, further comprising a display unit, which receives an inspection result from the paper-inspecting unit and displays the inspection result on a screen.

* * * * *